United States Patent [19]

Jacklich

[11] 4,184,490

[45] Jan. 22, 1980

[54] PRECISION ENDODONTIC SYRINGE

[76] Inventor: John Jacklich, c/o Continuing Education Consultants 102 Western Ct., Santa Cruz, Calif. 95060

[21] Appl. No.: 935,938

[22] Filed: Aug. 23, 1978

[51] Int. Cl.² ................................. A61M 1/00
[52] U.S. Cl. ................................. 128/236
[58] Field of Search ............... 128/236, 234, 218 R, 128/215, 216, 224

[56] References Cited

U.S. PATENT DOCUMENTS

| 951,160 | 3/1910 | Wainwright | 128/236 |
| 2,102,591 | 12/1937 | Hagemeier | 128/236 |
| 2,187,168 | 1/1940 | McAssey | 128/236 |

Primary Examiner—John D. Yasko
Attorney, Agent, or Firm—Robert G. Slick

[57] ABSTRACT

A precision endodontic syringe is provided of leak-proof construction which is adapted for precise injection of a paste root canal sealer into the apical part of root canal of a tooth as in root canal work.

2 Claims, 3 Drawing Figures

PRECISION ENDODONTIC SYRINGE

SUMMARY OF THE INVENTION

The present invention relates to a precision endodontic syringe which is adapted for the injection of a root canal sealer ordinarily a heavy paste into the root canal of a tooth as in root canal work.

Various syringes have been proposed in the past but they have not been fully satisfactory. In accordance with the present invention, a syringe is provided which has a fine threaded plunger thereon so that the amount of material which is injected can be precisely controlled.

Another objective of the invention is to provide a syringe of leak-proof construction. Certain prior art syringes are adapted for the injection of paste or semi-solid materials but will leak and not give precise results because of the leakage. The present invention employs a resilient ball which forms a tight fit in a mirror-smooth passage through a heavy walled cylinder, obviating the danger of leakage and permitting the syringe to be used with liquids as well as semi-solid materials without danger of breakage.

An object of the present invention is also to provide a reusable syringe which is easy to clean. The internal passage has a mirror-smooth surface and extends from one end of the barrel to the other and has no obstructions or crevices of any kind therein. Thus, the barrel can be easily swabbed completely clean as there are no crevices or the like which can collect foreign materials. Further, a replaceable ball is employed which acts as the sealing element within the syringe so that this can be discarded after a single usage.

Another object of the present invention is to provide a syringe that can be easily manufactured utilizing standard metal turning techniques, ordinary bar stock, eliminating the need of expensive molds and the like in fabricating a syringe.

Various other objects and advantages of the invention will be brought out in the balance of the specification.

DESCRIPTION OF THE PREFERRED EMBODIMENTS

Figure 1:
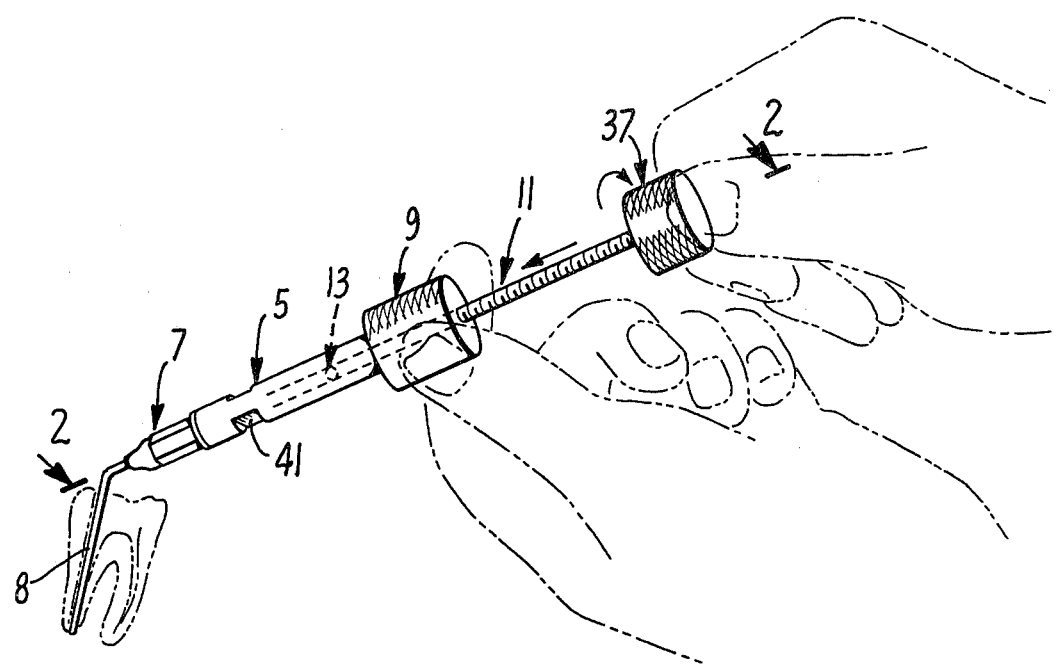
FIG. 1 is a perspective view of a syringe embodying the present invention.

Referring now to the drawings by reference characters, there is shown a syringe which includes a thick-walled stainless steel barrel, generally designated 5, a needle base 7, a cap 9, a threaded member 11, and a resilient ball 13.

The barrel 5 has a proximal end 15 and a distal end 17. The proximal end 15 has external threads 19 thereon and a smooth portion with no threads for ease in loading. The distal end 17 has a reduced diameter portion terminating in a shoulder 21 and having external threads 23 on the reduced diameter portion. The barrel includes a mirror-smooth inner cylindrical passage 25 which extends completely from one end to the other of the barrel.

Figure 2:
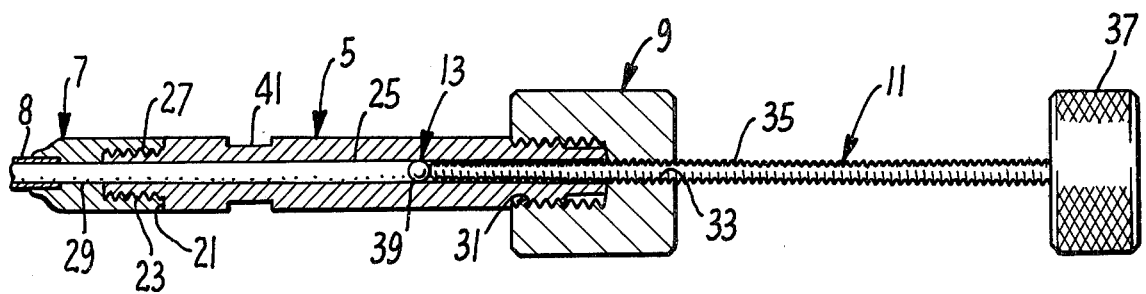
FIG. 2 is an enlarged section on the line 2—2 of FIG. 1.
Figure 3:
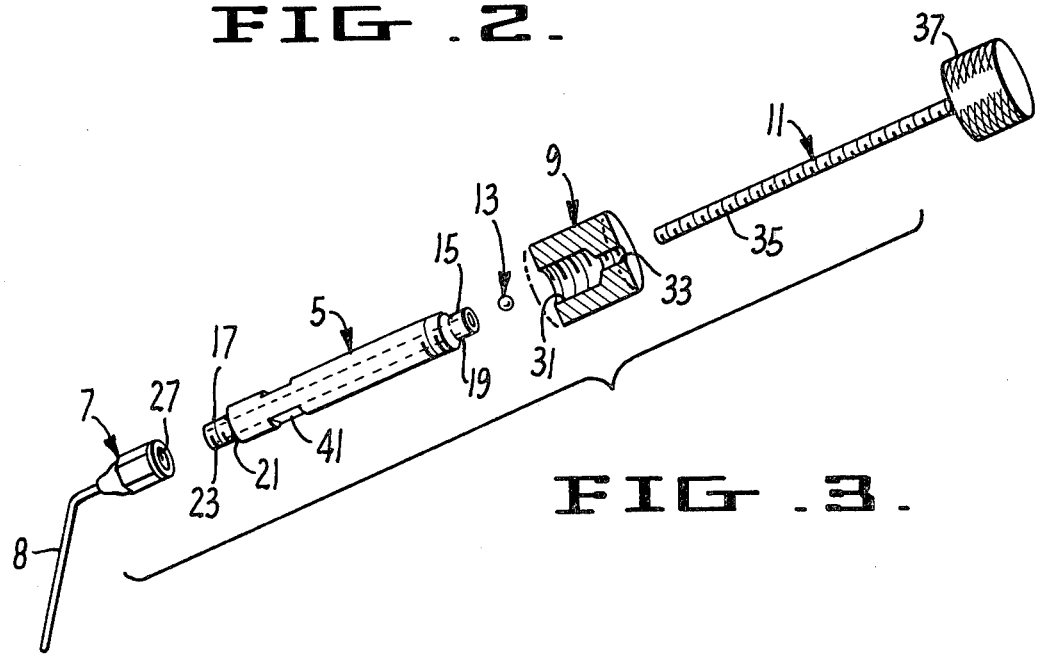
FIG. 3 is an exploded view of a syringe embodying the present invention.

The needle holder (hub) 7 has an internal passage 27 having threads to mate with threads 23 and further has a smooth passage 29 forming a smooth continuation of the passage 25 as is best seen in FIG. 2 The usual needle 8 is connected to the needle holder 7.

The cap 9 is larger in diameter than the barrel and has a first set of internal threads 31 adapted to mate with the threads 19. The cap also includes a second set of threads of reduced diameter designated 33 adapted to mate with the threaded member 11. The threaded member 11 has lands 35 which form a somewhat snug fit with the internal passage 25 of barrel 5. The proximal end of the threaded member 11 has a handle 37 thereon so that it can be easily grasped by the fingers and turned.

A resilient ball 39 forms a tight fit within the barrel 25. This ball 39 is made of an inert resilient plastic such as nylon or teflon and can be replaced after a single use.

Near the distal end of the barrel 5 are one or more flat spots 41 so that the barrel can be easily grasped by forceps.

It is believed apparent that the syringe described offers a number of advantages over syringes heretofore known. The needle base 17 and cap 9 are easily removed from the barrel without the use of a tool and ball 39 discarded. Since the passage 25 is continuous from one end of the barrel to the other, it is easy to swab out as there are no crevices to collect dirt or other residue. Since the parts are of metal in the preferred embodiment, they can be easily sterilized and will not explode under normal rise. Obvious, the threaded member 11 does not come in contact with the material being dispensed so that there is no possibility of the plunger causing contamination.

In addition the distance between 37 and 9 gives a reliable indication of the material remaining in the barrel 25.

I claim:

1. An endodonic syringe comprising in combination:
 a. a metal barrel of generally tubular shape having a proximal end and a distal end;
 b. a mirror-smooth, cylindrical internal passage extending for the entire length of said barrel;
 c. a reduced diameter portion on the external surface of the distal end;
 d. external threads of said reduced diameter portion;
 e. a needle base having an outer surface forming a continuation of the outer surface of said barrel;
 f. said needle base having internal threads mating with the external threads of paragraph d and having an internal cylindrical passage forming a continuation of the passage of paragraph b;
 g. external threads on the proximal end of said barrel;
 h. a cap on said proximal end having:
  (1) a first set of internal threads mating with the external threads of paragraph g and
  (2) a second set of internal threads of reduced diameter;
 i. a threaded member mating with and passing through and engaged with the threads of paragraph h (2), said threaded member extending beyond both ends of the cap, at one end into said cylindrical passage of paragraph b and at the other end beyond the end of the barrel of paragraph a, the lands of said threaded member being slightly smaller than the diameter of the cylindrical passage of paragraph b;
 j. a resilient loose ball snuggly fitting in said passage and adapted to being engaged by said threaded member and;
 k. handle means on the distal end of said threaded member to turn the same.

2. The structured claim 1 wherein the barrel has a flat spot on at least one side.

* * * * *